United States Patent [19]

Shima et al.

[11] Patent Number: 5,053,535

[45] Date of Patent: Oct. 1, 1991

[54] PROCESS FOR PRODUCING α-HYDROXYISOBUTYRIC ACID

[75] Inventors: Yoshikazu Shima; Takafumi Abe; Hirofumi Higuchi, all of Niigata; Koichi Kida, Tsukuba, all of Japan

[73] Assignee: Mitsubishi Gas Chemical Company, Inc., Tokyo, Japan

[21] Appl. No.: 618,058

[22] Filed: Nov. 23, 1990

[30] Foreign Application Priority Data

Mar. 26, 1990 [JP] Japan ................................ 2-73381

[51] Int. Cl.$^5$ ............................................. C07C 59/00
[52] U.S. Cl. ..................................... 562/579; 562/599
[58] Field of Search ............................................ 562/579

[56] References Cited

U.S. PATENT DOCUMENTS 2,971,981 2/1961 Aries .................................. 562/579

FOREIGN PATENT DOCUMENTS 1189972 4/1965 Fed. Rep. of Germany .
4226612 12/1967 Japan .................................. 562/579
4330289 12/1968 Japan .................................. 562/579
63-61932 11/1988 Japan .
1036289 7/1966 United Kingdom ................ 562/579

OTHER PUBLICATIONS

English Abstract of Japanese Publication 1-290650, Published 11/22/89.

Primary Examiner—Bruce Gray
Attorney, Agent, or Firm—Frishauf, Holtz, Goodman & Woodward

[57] ABSTRACT

A process for producing an α-hydroxyisobutyric acid which comprises hydrolyzing α-hydroxyisobutyric acid ester in the presence of an organic sulfonic acid catalyst, using an α-hydroxyisobutyric acid ester as the starting material.

According to said process, α-hydroxyisobutyric acid can be efficiently produced.

9 Claims, No Drawings

PROCESS FOR PRODUCING α-HYDROXYISOBUTYRIC ACID

BACKGROUND OF THE INVENTION

1. Field of the Invention

The present invention relates to a process for producing an α-hydroxyisobutyric acid. More particularly, it relates to a process for efficiently producing an α-hydroxyisobutyric acid by using an α-hydroxyisobutyric acid ester as the starting material. Since the α-hydroxyisobutyric acid is used as the starting material for producing methacrylic acid which is useful in industry, it is of great significance in industry to establish an economical process for producing α-hydroxyisobutyric acid.

2. Description of the Related Arts

As processes for preparing α-hydroxyisobutyric acid, (i) a process in which isobutylene is used as the starting material (German Patent No. 1,189,972), (ii) a process using isobutylene glycol as the starting material (J. Org. Chem., 23, 1488-9 (1958)), and (iii) a process in which acetone cyanohydrin, sulfuric acid and water are reacted and then subjected to hydrolysis (Japanese Patent Publication No. 61932/1988), have heretofore been known.

In the processes (i) and (ii), however, the yield of α-hydroxyisobutyric acid is insufficient, and a large amount of by-product is formed. Accordingly, if the total resultant of either process (i) or (ii) is used as the starting material, the yield of methacrylic acid as the final product comes to be greatly decreased. In the process (iii), the reaction solution contains acidic ammonium sulfate, so α-hydroxyisobutyric acid is difficult to be separated, and in addition, there is a problem of disposing of ammonium sulfate which results as by-product in at least an equal weight as that of the desired product, and accordingly, it is not an advantageous process for producing α-hydroxyisobutyric acid on an industrial scale.

SUMMARY OF THE INVENTION

The present inventors have intensively studied to establish an advantageous process for producing α-hydroxyisobutyric acid on an industrial scale. As the result, it was found that a high quality α-hydroxyisobutyric acid can be obtained in a high selectivity and yield by using α-hydroxyisobutyric acid ester as the starting material, and by hydrolyzing it in the presence of organic sulfonic acid catalyst, and thus the present invention was accomplished.

The present invention provides a process for producing an α-hydroxyisobutyric acid, which comprises hydrolyzing α-hydroxyisobutyric acid ester in the presence of an organic sulfonic acid catalyst.

DESCRIPTION OF PREFERRED EMBODIMENTS

The process of the present invention is described in more detail as follows.

The α-hydroxyisobutyric acid ester to be used in the present invention may be prepared by any process. For example, according to the process disclosed in Japanese Patent Application Laid-Open No. 290650/1989, α-hydroxyisobutyric acid ester can be easily prepared from α-hydroxyisobutyric acid amide and formic acid ester in the presence of a basic catalyst. In the process of the present invention, a preferred α-hydroxyisobutyric acid ester to be used as the starting material has an alkyl group with 1 to 8 carbon atoms, which constitutes the ester portion. Among α-hydroxyisobutyric acid ester, particularly preferred is methyl α-hydroxyisobutyrate.

Examples of the organic sulfonic acid catalysts to be used in the process of the present invention are organic sulfonic acids such as methanesulfonic acid and paratoluene-sulfonic acid, and organic sulfonic acids of high molecular weight such as strongly acidic ion-exchange resin. In view of separating the catalyst and the product, strongly acidic ion-exchange resin is particularly preferred, and with the help of it, a high quality α-hydroxyisobutyric acid can be obtained in a high selectivity and yield.

The strongly acidic ion-exchange resin catalyst to be used in the process of the present invention is not critical as long as it is styrene-divinylbenzene-based catalyst of sulfonic acid-type, but the preferred examples are Amberlite XH-105, DIAION RCP-145H, and Dowex 50 W-X8 (all are trade marks).

The reaction conditions in the process of the present invention are selected appropriately depending on the kind of the α-hydroxyisobutyric acid ester as the starting material or the kind of catalysts, but the reaction temperature should be 20° to 150° C., preferably 50° to 120° C., and the reaction period should be 5 minutes to 24 hours, preferably 10 minutes to 8 hours.

The molar ratio of water to α-hydroxyisobutyric acid ester in the process of the present invention is 1 to 100, but in consideration of energy consumption to be required for the separation after the reaction, it is preferably in the range of 1 to 10.

The reaction manner in the process of the present invention may be done in any way, so long as the process causes the starting material and the catalyst to contact.

Since the hydrolytic reaction in the process of the present invention is an equilibrium reaction, an effective way to raise the reaction rate is to distill away the alcohol formed as a by-product from the reaction system by means of reaction distillation and so on.

According to the process of the present invention as described above, α-hydroxyisobutyric acid having a high purity can be prepared easily in a high yield merely by separating the catalyst by a simple procedure from the reaction product solution after hydrolysis of α-hydroxyisobutyric acid ester, and subsequently by concentrating the reaction solution. If the reaction solution is distilled after the catalyst is separated, a still higher grade α-hydroxyisobutyric acid can be obtained. The catalyst recovered by separation is re-used in reaction without any special procedure, particularly when it is a strongly acidic ion-exchange resin.

In the process of the present invention, α-hydroxyisobutyric acid can be prepared under mild conditions and in a high selectivity and in a high yield, by using α-hydroxyiosbutyric acid ester as the starting material and an organic sulfonic acid catalyst as the catalyst.

Consequently, it has a great significance in that such an economical process for producing α-hydroxyisobutyric acid on an industrial scale has been established.

The present invention is described in greater detail with reference to the following examples, although it is not intended to be limited thereto.

EXAMPLE 1

In a 100 ml three-necked flask equipped with a distillation tube, a thermometer, and a stirrer, 60 g of aqueous solution of methyl α-hydroxyisobutyrate with a concentration of 33% by weight, and 2.0 g of strongly acidic ion exchange resin (Trade Mark: Amberlite XH-105, produced by Rohm & Haas Company) were placed, and reacted for 4 hours at a reaction temperature of 95° C. while methanol was being distilled away. As the result, the convention of methyl α-hydroxyisobutyrate was 99%, and the selectivity to α-hydroxyisobutyric acid was 99.9%.

COMPARATIVE EXAMPLE 1

The reaction was carried out in the same manner as in Example 1 except that 0.5 g of conc. sulfuric acid was added as a catalyst and the reaction period was 7 hours.

As the result, the conversion of methyl α-hydroxyisobutyrate was 94%, and the selectivity to α-hydroxyisobutyric acid was 68%.

EXAMPLE 2

The reaction was carried out in the same manner as in Example 1 except that 0.5 g of methanesulfonic acid was added as a catalyst and the reaction period was 2 hours.

As the result, the conversion of methyl α-hydroxyisobutyrate was 98%, and the selectivity to α-hydroxyisobutyric acid was 99%.

EXAMPLE 3

The same reaction was carried out as in Example 1 except that 1.0 g of paratoluenesulfonic acid was added as a catalyst, and the reaction period was 4 hours.

As the result, the conversion of methyl α-hydroxyisobutyrate was 98%, and the selectivity to α-hydroxyisobutyric acid was 99%.

EXAMPLE 4

The reaction was carried out in the same manner as in Example 1 except that 2.0 g of strongly acidic ion-exchange resin (Trade Mark: 50W-X8, produced by Dow Chemical Co.) was added as a catalyst, and the reaction period was 5 hours.

As the result, the conversion of methyl α-hydroxyisobutyrate was 99%, and the selectivity to α-hydroxyisobutyric acid was 99.8%.

EXAMPLE 5

In 100 ml three-necked flask equipped with a distillation tube, a thermometer, and a stirrer, 60 g of aqueous solution of ethyl α-hydroxyisobutyrate with a concentration of 50% by weight was placed, and 2.0 g of strongly acidic ion exchange resin (Trade Mark: DIAION RCP-145H, produced by Mitsubishi Kasei Industry Co., Ltd.) The mixture was reacted for 4 hours while the reaction temperature was maintained at 95° C. and ethanol was being distilled away.

As the result, the conversion of methyl α-hydroxyisobutyrate was 99%, and the selectivity to α-hydroxyisobutyric acid was 99.8%.

EXAMPLE 6

Sixty grams of 50% by weight aqueous solution of isopropyl α-hydroxyisobutyrate was placed into a 100 ml three-necked flask equipped with a distillation tube, a thermometer, and a stirrer, and then 2.0 g of strongly acidic ion exchange resin (Trade Mark: Amberlite XH-108, produced by Rohm & Haas Company) was added.

The reaction was continued for 6 hours while the reaction temperature was maintained at 95° C., and isopropanol was being distilled away.

As the result, the conversion of isopropyl α-hydroxyisobutyrate was 99%, and the selectivity to α-hydroxyisobutyric acid was 99.8%.

What is claimed is:

1. A process for producing an α-hydroxyisobutyric acid which comprises hydrolyzing α-hydroxyisobutyric acid ester in the presence of an organic sulfonic acid catalyst.

2. The process according to claim 1, wherein the organic sulfonic acid catalyst is a strongly acidic ion-exchange resin.

3. The process according to claim 2, wherein the strongly acidic ion-exchange resin is a styrene-divinylbenzene-based ion-exchange resin of sulfonic acid type.

4. The process according to claim 1, wherein the organic sulfonic acid catalyst is a methanesulfonic acid or parasulfonic acid.

5. The process according to claim 1, wherein α-hydroxyisobutyric acid ester is an ester having an alkyl group with 1 to 8 carbon atoms.

6. The process according to claim 1, wherein α-hydroxyisobutyric acid ester is methyl ester of α-hydroxyisobutyric acid.

7. The process according to claim 1, wherein the molar ratio of water is 1 to 100 to the α-hydroxyisobutyric acid ester.

8. The process according to claim 1, wherein the molar ratio of water is 1 to 10 to the α-hydroxyisobutyric acid ester.

9. The process according to claim 1, wherein the temperature of hydrolyzing reaction is 20° to 150° C., and the reaction period is 5 minutes to 24 hours.

* * * * *